US011116652B2

(12) United States Patent
Mojaver (10) Patent No.: US 11,116,652 B2
(45) Date of Patent: Sep. 14, 2021

(54) ORAL WEIGHT CONTROL DEVICE

(71) Applicant: Mahnaz Nina Mojaver, San Diego, CA (US)

(72) Inventor: Mahnaz Nina Mojaver, San Diego, CA (US)

(*) Notice: Subject to any disclaimer, the term of this patent is extended or adjusted under 35 U.S.C. 154(b) by 325 days.

(21) Appl. No.: 15/957,758

(22) Filed: Apr. 19, 2018

(65) Prior Publication Data

US 2018/0303647 A1    Oct. 25, 2018

Related U.S. Application Data

(63) Continuation-in-part of application No. 14/743,791, filed on Jun. 18, 2015, now abandoned.

(51) Int. Cl.
*A61F 5/56*    (2006.01)
*A61F 5/00*    (2006.01)

(52) U.S. Cl.
CPC .................. *A61F 5/0006* (2013.01)

(58) Field of Classification Search
CPC ........ A61F 5/0003; A61F 5/0006; A61F 5/56; A61F 5/566; A61F 2005/563; A61C 7/08; A61C 7/36
See application file for complete search history.

(56) References Cited

U.S. PATENT DOCUMENTS

| 4,455,138 | A |  | 6/1984 | Sheridan |
| 4,471,771 | A |  | 9/1984 | Brown et al. |
| 4,727,867 | A |  | 3/1988 | Knoderer |
| 4,738,259 | A |  | 4/1988 | Brown et al. |
| 6,138,679 | A |  | 10/2000 | Renders et al. |
| 6,390,812 | B1 | * | 5/2002 | Chishti ..................... A61C 7/00 433/6 |
| 9,180,034 | B1 | * | 11/2015 | Kapil ....................... A61C 7/00 |
| 2003/0059737 | A1 | * | 3/2003 | Hall ...................... A61F 5/0006 433/25 |
| 2003/0075186 | A1 |  | 4/2003 | Florman |

(Continued)

FOREIGN PATENT DOCUMENTS

| EP | 2735288 A1 | 5/2014 |
| WO | 2014153362 A1 | 9/2014 |

*Primary Examiner* — Ophelia A Hawthorne
*Assistant Examiner* — Camtu T Nguyen
(74) *Attorney, Agent, or Firm* — Avyno Law P.C.

(57) ABSTRACT

An oral weight control device that inhibits the mastication and swallowing of food is provided. The oral weight control device is a dental appliance that includes upper and lower retainers, where each retainer covers the lingual, palatal and buccal side of the teeth to inhibit mastication of food. The dental appliance further includes left and right flexible food barriers extending from the upper retainer to the lower retainer on the lingual side of the teeth to prevent food that a user may attempt to masticate between the upper and lower retainers from being passed to the tongue of the user to ingest. The upper and lower retainers may be customized to fit on each user and may cover all the upper and lower teeth of the wearer on the lingual, palatal and buccal sides of the teeth. The retainers may be removable or semi-permanently secured to the teeth. The flexible material is made of an elastic material and/or is sized to allow the jaws of the wearer to be fully opened and closed when the dental appliance is worn.

17 Claims, 5 Drawing Sheets

(56) References Cited

U.S. PATENT DOCUMENTS

| | | | |
|---|---|---|---|
| 2005/0075186 A1* | 4/2005 | Liao | A63B 69/3641 |
| | | | 473/259 |
| 2007/0048347 A1 | 3/2007 | Bardach et al. | |
| 2013/0230819 A1 | 9/2013 | Arruda | |
| 2014/0193767 A1* | 7/2014 | Li | A61C 7/14 |
| | | | 433/6 |
| 2015/0327956 A1* | 11/2015 | Mojaver | A61F 5/0006 |
| | | | 128/861 |

* cited by examiner

ORAL WEIGHT CONTROL DEVICE

RELATED APPLICATIONS

This is a continuation-in-part application, which claims priority to U.S. application Ser. No. 14/743,791, filed on Jun. 18, 2015, titled DENTAL APPLIANCE TO PREVENT MASTICATION, which application is incorporated in its entirety by reference in this application.

BACKGROUND OF THE INVENTION

1. Field of the Invention

The present invention relates to dental appliances and in particular, a dental appliance that inhibits a wearer's ability to masticate and swallow solid foods yet allows wearers to move their jaw.

2. Related Art

One of the most effective diets is the all liquid diet, which is based upon any appropriate liquid that contains all of the essential nutrients, without ingredients that add weight. The most difficult aspect of such a diet is the self-control required to prevent the eating of solid foods.

While there are other products currently on the market that inhibit the ingestion of solid foods, none of the other products on the market prevent the chewing of solid foods, which chewing is essential for the ingestion of solid foods. Such devices include U.S. Pat. No. 4,738,259 (the '259 patent) and U.S. Pat. No. 4,471,771 (the '771 patent) both of which teach are devices and method for disrupting natural mastication. The '259 patent is based upon the use of an outwardly projecting flange which is attached to a support collar, intended to make chewing more difficult. The device taught in the '259 patent does not completely block food from making contact with the tooth surfaces that are responsible for chewing and grinding solid food. In addition, the device taught by the '259 patent is extremely cumbersome and uncomfortable for the wearer and does not retain the teeth in their proper position. Further, the device can be removed by the wearer.

The '771 patent uses a net to capture certain foods while allowing other foods that are of smaller particle size to pass into the throat. This device has nothing to do with preventing food from being chewed. This device is awkward and uncomfortable and allows food to be trapped in the mouth.

Another device is taught by US20030075186 (Florman). This device restricts the distance the wearer can open the mouth. It does not prevent the chewing and swallowing of solid foods; however, it makes it quite difficult by preventing the user from opening his/her mouth.

Beside the discomfort and other down falls of the above described devices, all of the above devices affix to the teeth in a manner that can cause the teeth to shift. A need therefore exists for an oral weight control device that affixes to the teeth in a manner that prevents the teeth of the user from shifting and does not impede the movement of the jaw, thereby allowing the wearer to talk and open and close their mouths without restriction, all the while inhibiting the mastication and swallowing of solid foods.

SUMMARY

An oral weight control device that inhibits the mastication and swallowing of food is provided. The oral weight control device of the present invention is ideal for individuals following a liquid diet. As will be explained in further detail below, the oral weight control device is a dental appliance that is comfortable to the wearer and that allows full range of motion of the jaw. The wearer maintains the ability to fully open and close his/her mouth and perform all the functions of the mouth other than the chewing and swallowing of solid food.

The oral weight control device is a dental appliance that includes upper and lower retainers, where each retainer covers the lingual, palatal and buccal side of the teeth to inhibit mastication of food. The dental appliance further includes left and right flexible food barriers extending from the upper retainer to the lower retainer on the lingual side of the teeth to prevent food that a user may attempt to masticate between the upper and lower retainers from being passed to the tongue of the user to ingest. The upper and lower retainers may be customized to fit on each user and may cover all the upper and lower teeth of the wearer on the lingual, palatal and buccal sides of the teeth. The retainers may be removable or semi-permanently secured to the teeth. The flexible food barrier may be made of an elastic material and/or a material that is of a size to allow the jaws of the wearer to be fully opened and closed when the dental appliance is worn.

The upper and lower retainers (or retaining elements) may be secured to the teeth by dental cement or by buttons placed on the teeth that engage with corresponding recesses in the retainers. The dental cement provides a semi-permanent option for securing the retainers to the teeth of the wearer for those wearers that are more likely to remove the dental appliance and eat.

The upper and lower retainers may be secured to one or more teeth or may be customized to fit over all the teeth of the wearer. In all cases, the upper and lower retainers cover the lingual, buccal and palatal sides of the teeth, thereby retaining the teeth in their proper position at all times when the device is in place. Without a structure to retain the teeth in their proper position, the use of a device to restrict chewing or any other function of the jaws can result in teeth becoming misaligned.

In one example of an implementation, the flexible barrier is a sheet of solid elastic material or flexible material sized to allow the jaw to fully open and close. In other examples, the flexible barrier may be made of a plurality of individual strips attached to the upper and lower retainer elements and/or a semi-solid sheet of material (e.g. netting or other material having holes or perforations). The flexible barrier may further provide varying degrees of resistance to the wearer.

Other devices, apparatus, systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE FIGURES

The invention may be better understood by referring to the following figures. The components in the figures are not necessarily to scale, emphasis instead being placed upon illustrating the principles of the invention. In the figures, like reference numerals designate corresponding parts throughout the different views.

DETAILED DESCRIPTION

The present invention is based upon the manner in which the body processes solid foods for ingestion. When solid foods are taken into the mouth, the tongue automatically pushes the food onto the chewing surfaces of the premolars and molars. The present invention functions to interfere with the tongue's positioning of food on the teeth, thus preventing chewing and ingestion of solid food. In particular, the present invention frustrates the user's ability to chew and ingest solid foods by inhibiting food mastication and preventing any food that may be masticated by the premolars and molars from passing into the oral cavity inside the teeth to be swallowed. In summary, the present invention assists those on an all liquid diet to maintain their diet without the having to use willpower alone to refrain from eating solid foods and without impeding talking or opening and closing of one's mouth.

The invention accomplishes these objectives by (i) covering the teeth to prevent mastication and (2) placing a food barrier on the lingual side of the teeth between the teeth and the tongue. By covering the teeth with a retainer, the present invention is further able to prevent movement of the teeth, which commonly occurs with attaching devices that prevent the jaw from moving. Further, by using a flexible food barrier, movement of the jaw is not restricted like other devices on the market. Those skilled in the art will recognize that the barrier can be made from a number of shapes and that the barrier may be mounted to upper and lower retainers in a number of ways. Additionally, there are a number of materials that may be used to create a flexible barrier. For example, the barrier may be made of plastic, metal, nylon, etc. However, the preferred material is an elastomeric or soft plastic material. The barrier may stretch to allow for the mouth to substantially open and close. Alternatively, the barrier may be made of a flexible material sized to allow for the mouth to completely open and close. The barrier can also provide a variety of different degrees of resistance depending on the desires of the wearer.

Figure 1:
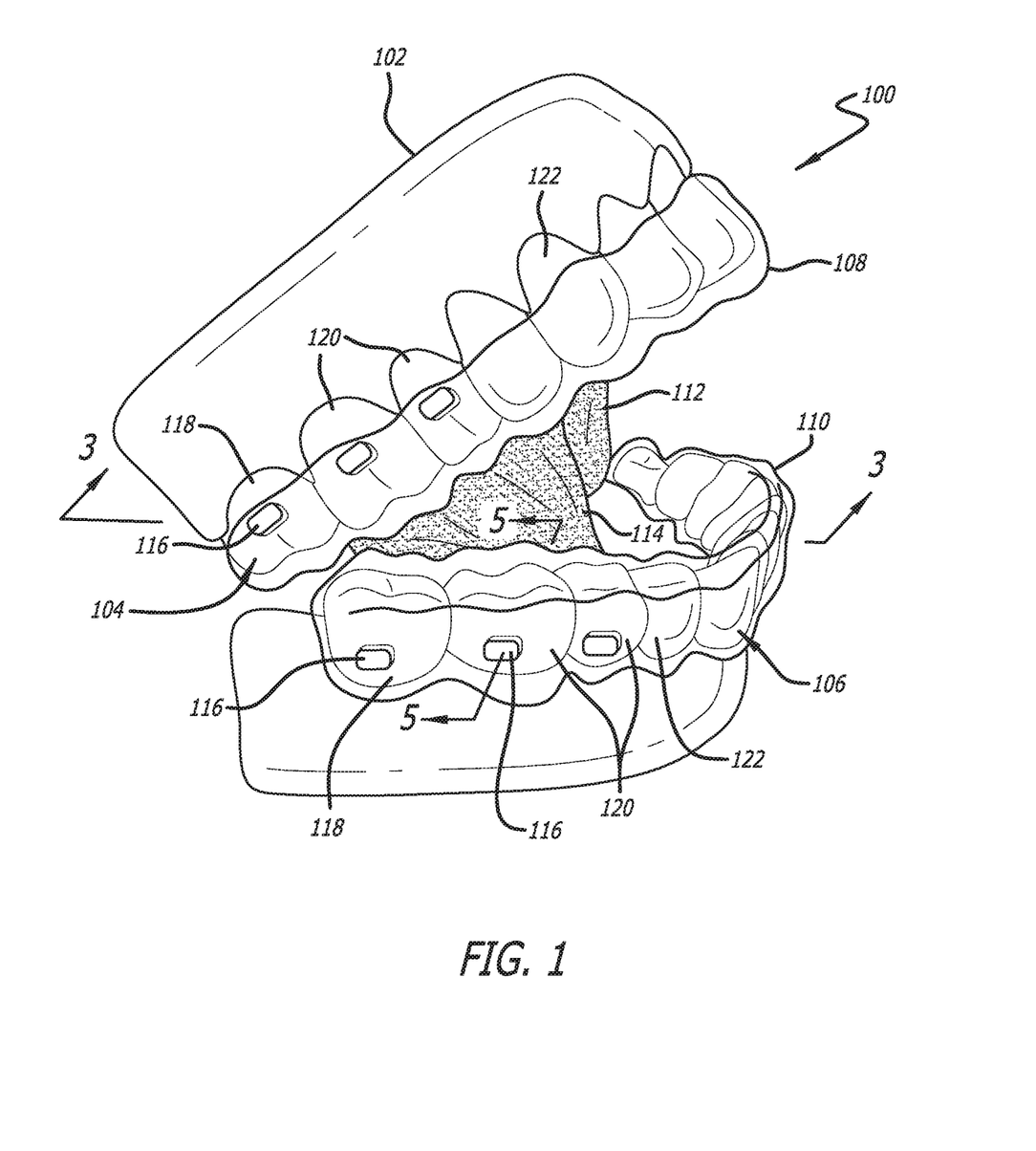
FIG. 1 is a perspective view of the right side of a mouth with the jaw in the open position, viewed from outside of the mouth and illustrating one example of an oral weight control device of the present invention.

FIG. 1 is a perspective view of the right side of a mouth 102 with the jaw in the open position, viewed from outside of the mouth 102 and illustrating one example of an oral weight control device of the present invention. As seen in FIG. 1, the oral weight control device is a dental appliance 100 that may be used to control weight. As illustrated, the dental appliance 100 in the present invention includes an upper retainer or retaining element 108 covering the upper teeth 104 and a lower retainer 110 covering the lower teeth 106. Attached to and extending between the upper retainer 108 and the lower retainer 110 are left and right food barriers 112, 114.

The food barriers 112, 114 are positioned on the lingual side of the upper and lower teeth 104, 106 and are affixed to the upper and lower retainers 108, 110. As illustrated, the upper retainer 108 and lower retainer 110 may cover the buccal and lingual sides of the teeth 104, 106. The lingual side of a tooth is the inner surface of the tooth that faces the tongue or the oral cavity of the mouth. The buccal side is the side of a tooth is the side that faces the inside of the cheek. While the examples illustrate that the upper and lower retainers 108, 110 cover all the upper and lower teeth 104, 106. The retainers 108, 110 may also be designed to cover only a few teeth 104, 106, such as one or more of the molars 118, premolars 120 and/or canine teeth 122. Further, the retainers 108, 110 may be customized for a user by taking molds of a user's teeth 104, 106 or by providing moldable retainers. Alternatively, the retainers 108, 110 may simply be trays that cover one or more, or all of the teeth 104, 106.

In one example, the upper retainer 108 and a lower retainer 110 may be retained against the upper teeth 104 and lower teeth 106 using buttons 116 placed on the teeth 104, 106 that correspond to recesses in upper and lower retainers 108, 110. The buttons 116 may be placed on the lingual or buccal side of the teeth 104, 106, or both. Further, buttons 116 may be placed on one, more than one, or all of the molars 118, premolars/bicuspids 120 and/or canine teeth 122. The food barriers 112, 114 may extend horizontally from the molars 118 across the premolars 120 on both sides of the mouth. Optionally, the food barriers 112 and 114 may extend from the molars 118 to the canine 122 teeth on both sides of the mouth 102.

Figure 2:
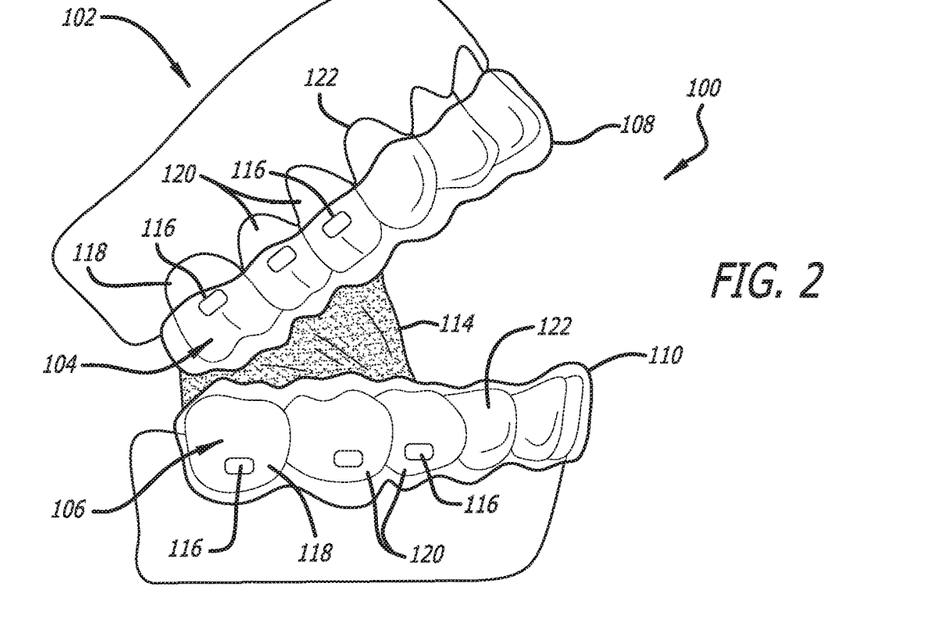
FIG. 2 is a side view of the right side of the mouth of FIG. 1 illustrating the oral weight control device of FIG. 1.

FIG. 2 is a side view of the right side of the mouth 102 of FIG. 1. FIG. 2 best illustrates the food barrier 114 on the right side of the mouth 102 extending from the molar 118 across the premolars 120. As seen in FIG. 2, food placed on the chewing surface of the molars 118 and premolars 120 would not be able to pass into the oral cavity of the mouth to be ingested to due food barrier 114.

The left and right food barriers 112, 114 are made of a flexible material, such as an elastomeric material, which will not impede the jaw from moving. When the food barriers 112, 114 are made of an elastic material, the food barriers 112, 114 can be stretched when the jaw is opened. Alternatively, the flexible material may not be elastic, but may be bendable and of a size that permits the jaw to freely move. By not impeding the movement of the jaw, the wearer may be able to talk and open and close his or her mouth without restriction unlike other oral weight control devices.

Figure 3:
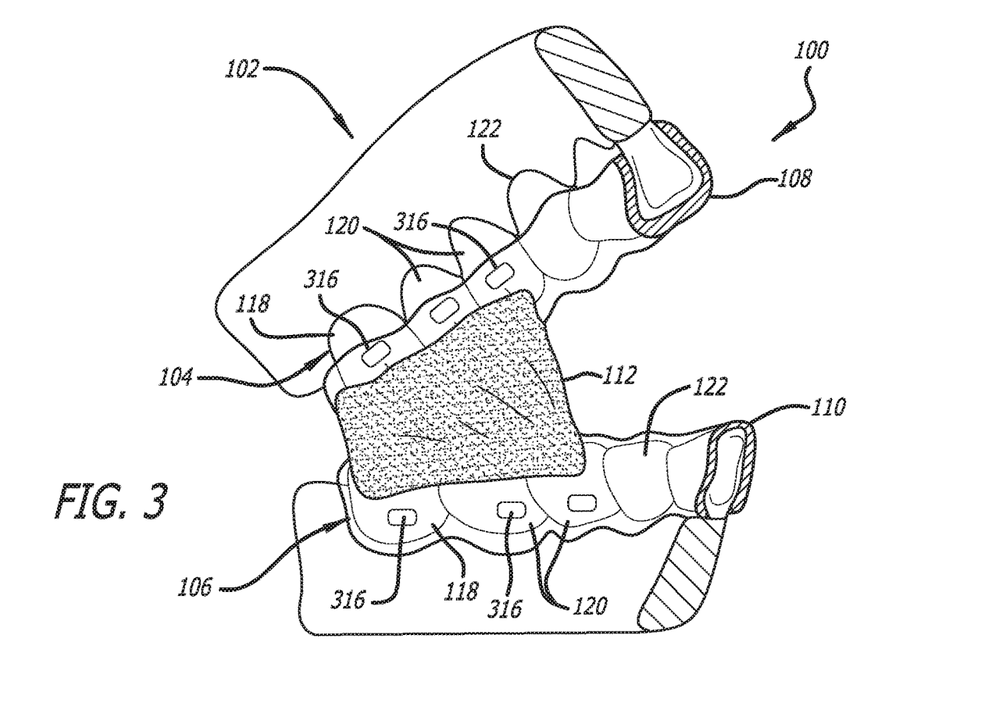
FIG. 3 is a cross-section of taken along line 3-3 of FIG. 1 illustrating the left food barrier of the oral weight control device attached to upper and lower retainer elements on the lingual side of the teeth.

FIG. 3 is a cross-section taken along line 3-3 of FIG. 1. FIG. 3 illustrates the left food barrier 112 attached to upper and lower retainers 108, 110 on the lingual side of the teeth 104, 106. FIG. 3 best illustrates the attachment of the left food barrier 112 to the upper and lower retainers 104, 106 or retaining elements. The food barrier 112 has an upper end attached to the upper retainer 104 and a lower end attached to the lower retainer 106. The opposing ends of the food barrier 112 may be attached to the upper and lower retainers 104, 106 using any commonly known attachment mechanism, such as adhesive, tacking or stapling.

As illustrated, the food barrier 112 in this example is a solid thin sheet of elastomeric material which is affixed at its top and bottom across the upper and lower retainers 108 and 110 extending from the molar 118 across both premolars 120. As mentioned previously, the food barrier 112 may also be extended and affixed to the upper and lower canines 122 for a fuller barrier. Again, by attaching the food barrier 112 to the interior lingual side of the retaining elements 108, 110, the food barrier 112 prevents any food that may be masticated between the upper and lower teeth 104, 106, on their chewing surface, from passing into the user's oral cavity to swallow.

While the retaining elements 108, 110 do function to inhibit a user's ability to masticate food, the barriers 112, 114 prevent any food that the user attempts to masticate from entering the oral cavity interior to the teeth of the user, to be ingested. As illustrated in FIGS. 1-3, the dental appliance 100 functions as an oral weight control device that inhibits the user's ability not only to masticate food by having the upper retainer and lower retainer 108, 112 covering the lingual, buccal and chewing surfaces of the teeth 104, 106, but also prevents any food that is masticated from passing into the interior of the user's mouth by the food barriers 112, 114.

Figure 4:
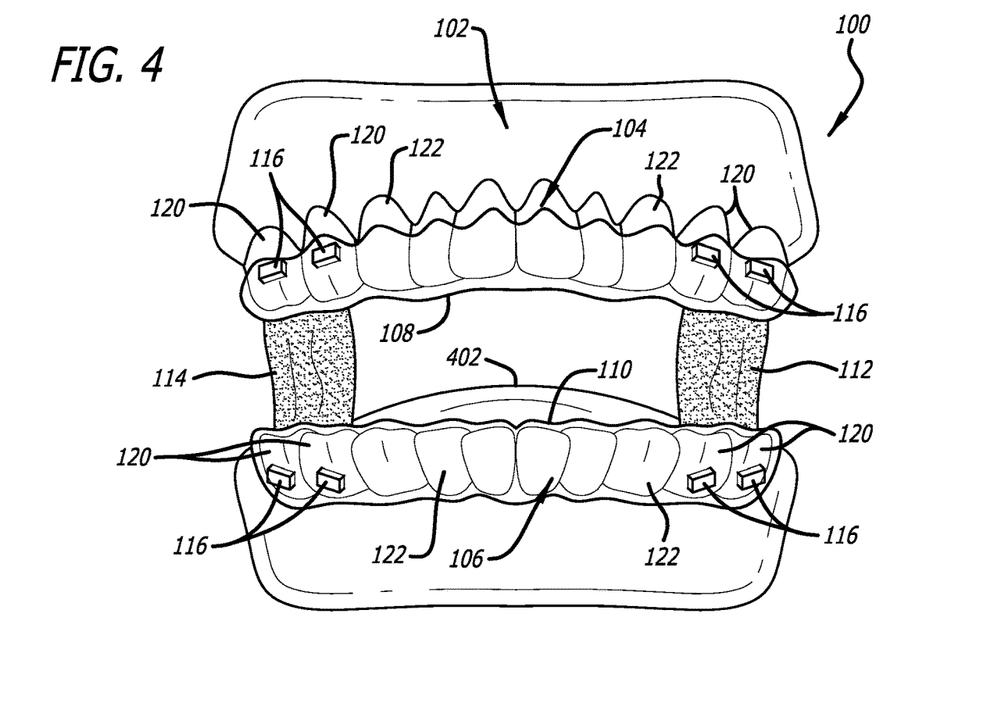
FIG. 4 is a front view of the mouth in an open position illustrating the oral weight control device of the present invention.

FIG. 4 is a front view of the mouth 102 in an open position with left and right side food barriers 112, 114 attached to the upper and lower retainer elements 108, 110 on the lingual side of the teeth 104, 106. FIG. 4 best illustrates the positioning of the left and right food barriers 112, 114 relative to the wearer's tongue 402. FIG. 4 further highlights the inability of the user when masticating food between the retaining elements 108, 110, as permissible, from being able to transfer the food to the interior of the mouth 102 to swallow. As can also be seen in FIG. 4, the food barriers 112, 114 are very thin so as to ensure maximum comfort. As set forth in more detail above, while the retainer elements 108, 110 are shown covering all the teeth 104, 106, the retainer elements 108, 110 may in fact be designed to cover only a portion of the teeth 104, 106.

Figure 5:
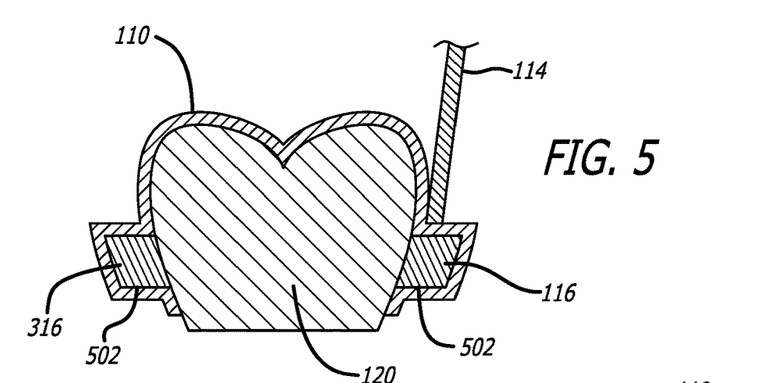
FIG. 5 is a cross sectional view of a tooth taken along line 5-5 of FIG. 1 showing one example of a mechanism for attaching the oral weight control device to the teeth of the wearer.

FIG. 5 is a cross section of a tooth taken along line 5-5 of FIG. 1, showing one example of an option for attaching retainers 108, 110 to the teeth 104, 106. The cross-section is taken across premolar 120 and illustrates one example of how the lower retaining element 110 may be secured against a tooth. As illustrated, buttons 116, 316 may be affixed to the tooth, for example, using dental cement. The buttons 116, 316 may be positioned on the lingual and buccal side of the tooth 120. Button 116 is shown positioned on the buccal side of the tooth, whereas button 316 is shown positioned on the lingual side of the tooth 120. The retaining element 110 is designed to have recesses 502 for receiving the buttons 116, 316 to retain the retaining element 110 against the tooth 120. The barrier 114 is then attached to the lingual side of the retaining element 110. While this method for affixing the retaining element 110 is shown with respect to only one tooth 120, as illustrated in FIGS. 1-4, the method for affixing the retaining element 110 to the teeth 104, 106 may be applied to any number of teeth 104, 106.

Figure 6:
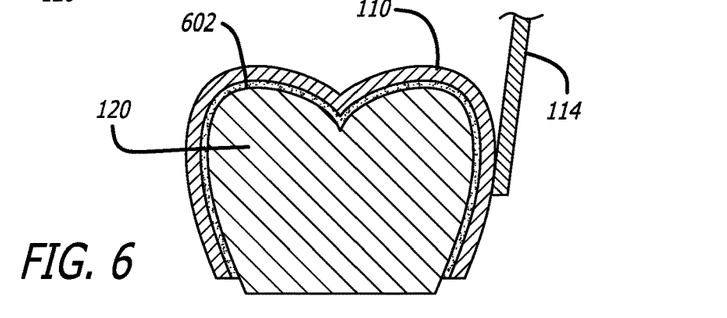
FIG. 6 is a cross sectional view of a tooth showing another example of a mechanism for attaching the oral weight control device to the teeth of the wearer.

FIG. 6 is a cross section of a tooth showing another example of an option for attaching the retainer elements 110 to the tooth 120. FIG. 6 illustrates a more permanent, or semi-permanent, way to affix a retaining element 110 to a tooth 120. As illustrated in FIG. 6, the retaining element 110 may be affixed to the tooth 120 using an adhesive, for example, dental cement 602. The dental cement 602 affixes the retaining element 110 to the tooth 120 making it difficult for the user to remove the retaining element 110 without the assistance of a dentist. This more permanent way to secure the retaining element 110 to the teeth may be more desirable for those with less willpower to keep the dental appliance affixed to teeth at all times.

While the dental cement 602 is shown applied on the lingual, buccal and chewing surface of the tooth 602, it may not be necessary to apply the dental cement 602 to cover the entire tooth 120. Further, the dental cement 602, when affixing the retainers 108, 110 to the teeth 104, 106, may not be applied to all the teeth, it can be applied to one, more or all the teeth 104, 106 as deemed appropriate to protect the teeth from food entering under the retainers 108, 110 or as needed to retain the retainers 108, 110 against the teeth 104, 106. As illustrated in FIG. 6, right food barrier 114 is also shown affixed to the lingual side of the retaining element 110. While FIGS. 5 and 6 show buttons 116, 316 and dental cement 602 used separately, in another example, the buttons 116, 316 and dental cement 602 may be used together to provide additional strength for securing the retaining elements 108, 110 to the teeth.

Figure 7:
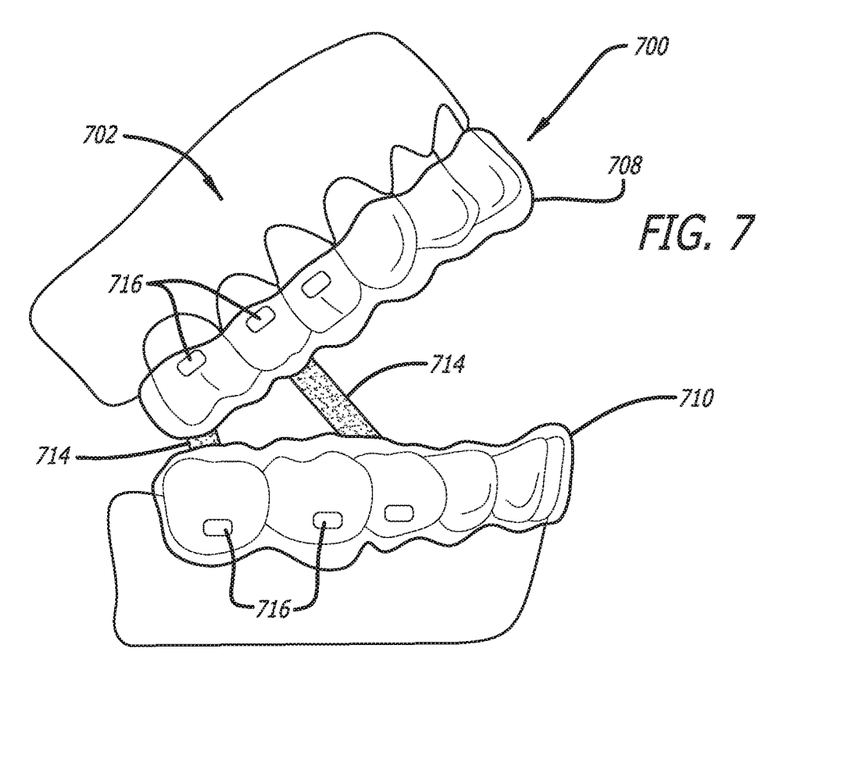
FIG. 7 is a side perspective view of the right side of the mouth with the jaws in the open position illustrating another example of an oral weight control device of the present invention.

FIG. 7 is a side perspective view of the right side of the mouth with the jaws in the open position illustrating another example of a food barrier 714 that may be attached to upper and lower retainer elements 708, 710 on the lingual side of the teeth. Similar to food barriers 112, 114, food barrier 714 may be made of a flexible material, such as an elastomeric material, which will not impede the jaw from moving. As illustrated in FIG. 7, the retaining element 714 may be a plurality of strips rather than a solid sheet food barrier 112, 114 as illustrated in FIGS. 1-5. In this example, some food will or could be allowed to pass into the user's oral cavity to swallow; however, the amount of food that is able to pass into the user's oral cavity to swallow will still be minimized. Further, the upper and lower retaining elements 108, 110 still prevent mastication and the strips 714 still prevent food from some food from passing in to the interior of the user's mouth. The strips 714 further prevent the tongue from moving food onto the chewing surfaces of the teeth and back onto the tongue once masticated.

Figure 8:
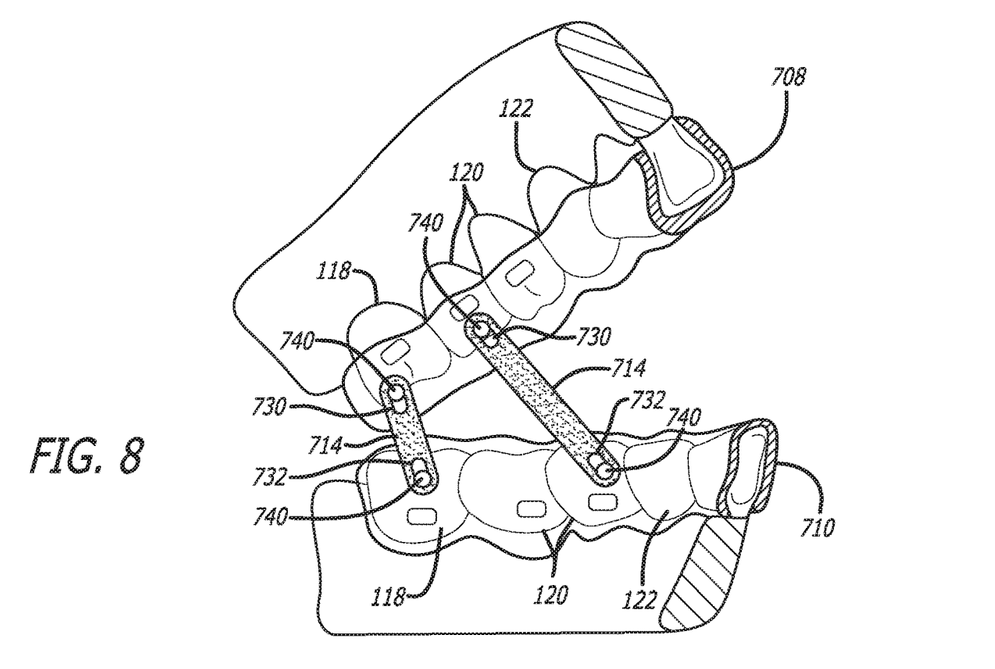
FIG. 8 is a cross-sectional view taken along line 8-8 of FIG. 9 illustrating the left food barrier attached to upper and lower retainer elements on the lingual side of the teeth.
Figure 9:
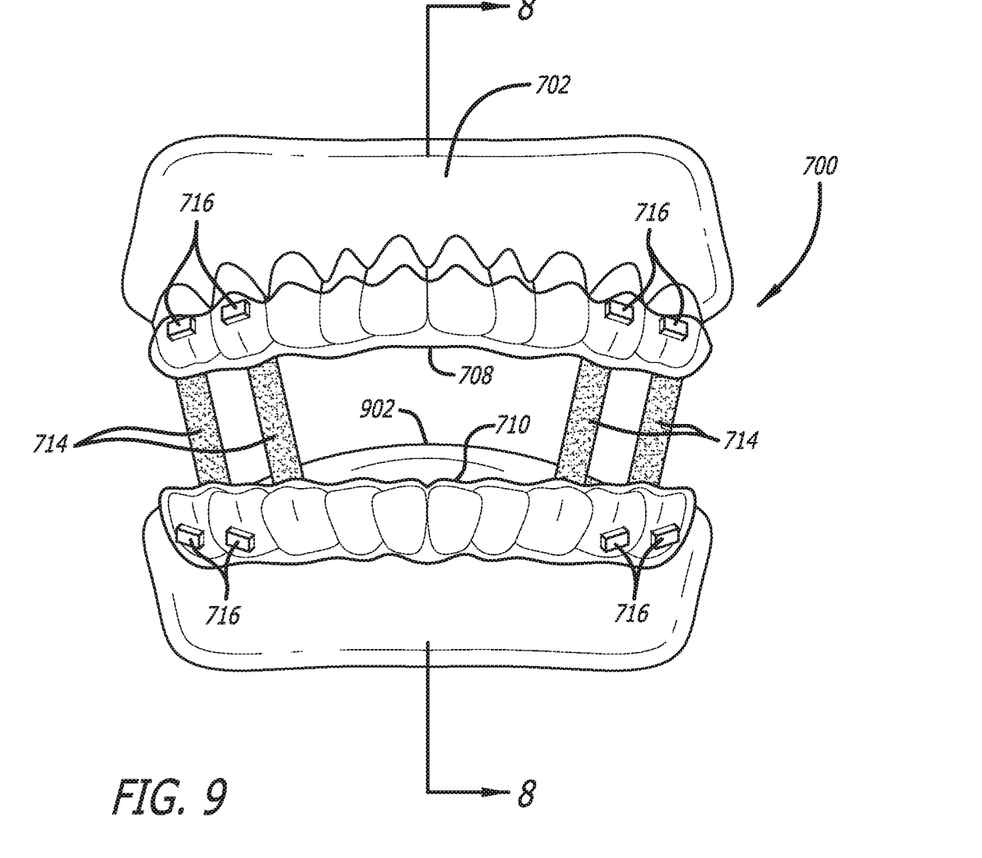
FIG. 9 is a front view of the mouth in an open position with left and right side food barriers of FIG. 7 attached to the upper and lower retainer elements on the lingual side of the teeth.

FIG. 8 is a cross-section taken along line 8-8 of FIG. 9 illustrating the left food barrier 714 attached to upper and lower retainer elements 708, 710 on the lingual side of the teeth. The plurality of strips of the food barrier 714 may include upper slits 730 located on the top of the plurality of strips 714 and lower slits 732 located on the bottom of the plurality of strips 714. The upper and lower slits 730, 732 may engage with pegs or hooks 740 positioned on the lingual side of the upper and lower retaining elements 708, 710. The pegs or hooks 740 may be attached to the upper and lower retainers 104, 106 using any commonly known attachment mechanism, such as dental cement. While FIG. 8 shows the pegs or hooks 740 located on the upper and lower retaining elements 708, 710 in front of the lingual side of the upper and lower molars 118 and upper and lower premolars 120, any number of pegs or hooks 740 can be located on the lingual side on any number of upper or lower molars 118, premolars 120 or canines 122. Similarly, while FIG. 8 shows food barrier 714 being two strips, any number of strips may be affixed to the upper and lower retaining elements 708, 710 to provide a fuller barrier. Additionally, the pegs or hooks 740 may be located in any location on the lingual side of the teeth as desired by the wearer.

Again, by attaching the food barrier 714 to the interior lingual side of the retaining elements 708, 710, the food barrier 714 prevents any food that may be masticated between the upper and lower teeth, on their chewing surface, from passing into the user's oral cavity to swallow.

FIG. 9 is a front view of the mouth 702 in an open position with left and right side food barriers 714 attached to the upper and lower retainer elements 708, 710 on the lingual side of the teeth. FIG. 9 best illustrates the positioning of the left and right food barriers 714 relative to the wearer's tongue 902. FIG. 9 further highlights the inability of the user when masticating food between the retaining elements 708, 710, as permissible, from being able to transfer the food to the interior of the mouth 702 to swallow. As can also be seen in FIG. 9, the food barrier 714 may be very thin so as to ensure maximum comfort. As set forth in more detail above, while the retainer elements 708, 710 are shown covering all the teeth, the retainer elements 708, 710 may in fact be designed to cover only a portion of the teeth.

Any or all food barriers 112, 114, 714 and/or retaining elements 108, 110, 708, 710 or other elements of the device, including but not limited to buttons 116, 316, pegs 740 and/or adhesive, may be transparent, may be a solid color or may include designs or other ornate features.

While the invention herein disclosed has been described by means of specific embodiments and applications thereof, numerous modifications and variations could be made thereto by those skilled in the art without departing from the spirit and scope of the appended claims, the invention may be practiced otherwise than as specifically described herein.

The foregoing description of implementations has been presented for purposes of illustration and description. It is not exhaustive and does not limit the claimed inventions to the precise form disclosed. Modifications and variations are possible in light of the above description or may be acquired from practicing the invention. The claims and their equivalents define the scope of the invention.

It will be understood that various aspects or details of the invention may be changed without departing from the scope of the invention. Furthermore, the foregoing description is for the purpose of illustration only, and not for the purpose of limitation—the invention being defined by the claims.

I claim:

1. An oral weight control device for attachment to teeth within a mouth of a user for inhibiting the user's ability to masticate and swallow solid foods yet allowing the user to move the user's jaw, said oral weight control device comprising:
    an upper retaining element for attachment to two or more upper teeth within the mouth of the user, the upper retaining element being shaped such that it is capable of substantially covering the buccal side and lingual side of the two or more upper teeth when the upper retaining element is affixed to the two or more upper teeth of the user, whereby the upper retaining element, when affixed to the two or more upper teeth of the user, is capable of retaining the two or more upper teeth in their proper positions, and whereby at least one button is further provided that is capable of being positioned on the two or more teeth and whereby the upper retaining element includes at least one recess for engaging the at least one button to retain the upper retaining element against the two or more upper teeth of the user;
    a lower retaining element for attachment to two or more lower teeth within the mouth of the user, the lower retaining element being shaped such that it is capable of substantially covering the buccal side, lingual side and palatal side of the two or more lower teeth when the lower retaining element is affixed to the two or more lower teeth of the user, whereby the lower retaining element, when affixed to the two or more lower teeth of the user, is capable of retaining the two or more lower teeth in their proper positions and when worn with the upper retaining element inhibit mastication of food, and whereby at least one button is further provided that is capable of being positioned on the two or more teeth include and whereby the lower retaining element includes at least one recess for engaging the at least one button to retain the lower retaining element against the two or more lower teeth of the user;
    a flexible food barrier having an upper end and a lower end, said upper end of the flexible food barrier being attached to the upper retaining element and said lower end of the flexible food barrier being attached to the lower retaining element, whereby the flexible food barrier is a thin elastic sheet that, when positioned within the user's mouth, is adapted to rest between the tongue and the lingual side of the teeth in the mouth of the user and extend from the molars to the premolars, thereby inhibiting solid food placed in the user's mouth from easily reaching the tongue of the user from the food chewing surface of the teeth, to block food masticated on the chewing surface of the molars from passing to the tongue of the user and to impede the swallowing of solid food without impeding jaw movement.

2. The oral weight control device of claim 1, further includes an adhesive for securing the upper retaining element to two or more upper teeth of the user and for securing the lower retaining element to two or more lower teeth of the user.

3. The oral weight control device of claim 1, wherein the flexible food barrier is affixed to the upper and lower retaining elements by tacking the flexible food barrier to the retaining elements.

4. The oral weight control device of claim 1, wherein the flexible food barrier is affixed to the upper and lower retaining elements with adhesive.

5. An oral weight control device for attachment to teeth within a mouth of a user for inhibiting the user's ability to masticate and swallow solid foods yet allowing the user to move the user's jaw, said oral weight control device comprising:
    an upper retaining element for attachment to two or more upper teeth within the mouth of the user, the upper retaining element being shaped such that it is capable of substantially covering the buccal side and lingual side of the two or more upper teeth when the upper retaining element is affixed to the two or more upper teeth of the user, whereby the upper retaining element, when affixed to the two or more upper teeth of the user, is capable of retaining the two or more upper teeth in their proper positions, and whereby adhesive is used to make the upper retaining element capable of being is secured to the two or more lower teeth of user;
    a lower retaining element for attachment to two or more lower teeth within the mouth of the user, the lower retaining element being shaped such that it is capable of substantially covering the buccal side, lingual side and palatal side of the two or more lower teeth when the lower retaining element is affixed to the two or more lower teeth of the user, whereby the lower retaining element, when affixed to the two or more lower teeth of the user, is capable of retaining the two or more lower teeth in their proper positions and when worn with the upper retaining element inhibit mastication of food, and whereby adhesive is used to make the lower retaining element capable of being is secured to the two or more lower teeth of user;

a flexible food barrier having an upper end and a lower end, said upper end of the flexible food barrier being attached to the upper retaining element and said lower end of the flexible food barrier being attached to the lower retaining element, whereby the flexible food barrier is a thin elastic sheet that, when positioned within the user's mouth, is adapted to rest between the tongue and the lingual side of the teeth in the mouth of the user and extend from the molars to the premolars, thereby inhibiting solid food placed in the user's mouth from easily reaching the tongue of the user from the food chewing surface of the teeth, to block food masticated on the chewing surface of the molars from passing to the tongue of the user and to impede the swallowing of solid food without impeding jaw movement.

6. The oral weight control device of claim 5, wherein the flexible food barrier is affixed to the upper and lower retaining elements with adhesive.

7. The oral weight control device of claim 5, wherein the flexible food barrier is affixed to the upper and lower retaining elements by tacking the flexible food barrier to the retaining elements.

8. The oral weight control device of claim 5, where the adhesive is dental cement.

9. An oral weight control device for attachment to teeth within a mouth of a user inhibiting the user's ability to masticate and swallow solid foods yet allowing the user to move the user's jaw, said oral weight control device comprising:

an upper retaining element for attachment to the upper teeth within the mouth of the user, the upper retaining element being shaped such that it is capable of substantially covering the buccal and lingual side of all the upper teeth of the user when the upper retaining element is affixed to the upper teeth of the user, whereby the upper retaining element, when affixed to the upper teeth of the user, is capable of retaining the upper teeth in their proper positions;

a lower retaining element for attachment to the lower teeth within the mouth of the user, the lower retaining element being shaped such that it is capable of substantially covering the buccal and lingual side of all the lower teeth when the lower retaining element is affixed to the lower teeth of the user, whereby the lower retaining element, when affixed to the lower teeth of the user, is capable of retaining the lower teeth in their proper positions and when worn with the upper retaining element inhibit mastication of food;

a first and second flexible food barrier;

the first food barrier having an upper end and a lower end, where the upper end of the first flexible food barriers is attached to the right lingual side of the upper retaining element and the lower end of the flexible food barrier being attached to the right lingual side of the lower retaining element;

the second food barrier having an upper end and a lower end, where the upper end of the second flexible food barriers is attached to the left lingual side of the upper retaining element and the lower end of the flexible food barrier being attached to the left lingual side of the lower retaining element;

whereby the first and second flexible food barriers are each thin elastic sheets that, when positioned within theft user's mouth, are adapted to rest between the tongue and the right and left lingual sides of the teeth in the mouth of the user and extend from the molars to the premolars, thereby inhibiting solid food placed in the user's mouth from easily reaching the tongue of the user from the food chewing surface of the teeth to block food masticated on the chewing surface of the molars from passing to the tongue of the user and to impede the swallowing of solid food without impeding jaw movement.

10. The oral weight control device of claim 9 where at least one button is further provided that is capable of being positioned on two or more of the upper teeth and whereby the upper retaining element includes at least one recess for engaging the at least one button to retain the upper retaining element against the upper teeth of the user.

11. The oral weight control device of claim 9, where at least one button is further provided that is capable of being positioned on two or more of the lower teeth and whereby the lower retaining element includes at least one recess for engaging the at least one button to retain the lower retaining element against the lower teeth of the user.

12. The oral weight control device of claim 9 where adhesive is used to make the upper and lower retaining elements capable of being secured to the upper and lower teeth of the user.

13. The oral weight control device of claim 12 where the adhesive is dental cement.

14. The oral weight control device of claim 9 where the upper and lower retaining elements are custom designed such that are capable of fitting a particular user's teeth.

15. The oral weight control device of claim 9 where the upper and lower retaining elements are dental trays that cover the teeth.

16. The oral weight control device of claim 9, wherein the first and second flexible food barriers are affixed to the upper and lower retaining elements with adhesive.

17. The oral weight control device of claim 9, wherein the first and second flexible food barrier are affixed to the upper and lower retaining elements by tacking the first and second flexible food barriers to the retaining elements.

* * * * *